US00PP10602P

United States Patent [19]

Akerboom

[11] Patent Number: Plant 10,602

[45] Date of Patent: Sep. 15, 1998

[54] ASTER PLANT NAMED 'MILKA'

[75] Inventor: Petrus J. Akerboom, Ter Aar, Netherlands

[73] Assignee: De Nachtvlinder B.V., Ter Aar, Netherlands

[21] Appl. No.: 664,519

[22] Filed: Jun. 17, 1996

[51] Int. Cl.[6] ..... A01H 5/00

[52] U.S. Cl. ..... Plt./68.1

[58] Field of Search ..... Plt./68.1

[56] References Cited

PUBLICATIONS

UPOVROM Disk 1996 Feb. Search Results 3 pages.

*Primary Examiner*—Howard J. Locker
*Assistant Examiner*—Kent L. Bell
*Attorney, Agent, or Firm*—Foley & Lardner

[57] ABSTRACT

The new aster variety 'Milka' is very short to short in height as flowering commences; produces leaves that are elliptic in shape, medium to long in length, and dark green in color; and has a flower head with many ray florets that are purple in color and are narrowly elliptic in shape.

2 Drawing Sheets

The present invention comprises a new and distinct cultivar of Aster plant hereinafter referred to by the cultivar name 'Milka'.

The new cultivar was originated from a cross made by the inventor in a controlled breeding program in Ter Aar, The Netherlands. The female or seed parent was a selection from proprietary breeding stock designated the "Butterfly family" while the male or pollen parent was a selection from proprietary breeding stock designated the "P" family.

'Milka' was discovered and selected by the inventor as a flowering plant within the progeny of the stated cross in a controlled environment in Ter Aar, The Netherlands. Asexual reproduction of the new cultivar, by cuttings, as performed by applicant for the first time in April 1993 in Ter Aar, The Netherlands, and continuing thereafter, has demonstrated that the combination of characteristics as herein disclosed for the new cultivar are firmly fixed and retained through successive generations of asexual reproduction.

'Milka' has not been observed under all possible environmental conditions. The phenotype may vary with variations in environmental conditions such as temperature, light intensity and day length, without a change in the genotype of the plant. The following observations, measurements and values describe the new cultivar as grown in Bet Dagan, Israel under conditions which closely approximate those generally used in commercial practice.

The following traits have been repeatedly observed and are determined to be basic characteristics of 'Milka' which in combination distinguish this aster as a new and distinct cultivar:

1. 'Milka' is very short to short in height as flowering commences.
2. The leaves produced by 'Milka' are elliptic in shape, medium to long in length and are dark green in color without anthocyanin coloration.
3. The first flower heads produced are spread along the axis.
4. The flower head is medium to large in size with many ray florets.
5. The ray florets are medium to long in size and narrowly elliptic in shape.
6. The involucre is cylindrical in shape and very long.
7. Flowering commences very late compared to other asters.

The new cultivar is most similar to 'Karmijn' (U.S. plant patent application Ser. No. 08/664,520) and 'Parade' (U.S. plant patent application Ser. No. 08/664,669), both of which are described in co-pending applications of the inventor. All of these cultivars produce flowers with numerous ray florets and a similar type of flower head. These cultivars differ, however, with respect to flower color, plant height and leaf length.

The following Table provides several phenotypic characteristics that can be used to distinguish the aster varieties 'Parade', 'Milka' and 'Karmijn'.

| | Ray Florets | | | Capitulum | |
|---|---|---|---|---|---|
| | Colors (RHS) | Length (mm) | Diameter (mm) | Diameter (mm) | Involucre Shape |
| 'Parade' | Purple (87A) | 11–13 | 1.8 | 28–30 | Funnel-shaped, Long |
| 'Milka' | Violet (85A) | 14–16 | 2.0 | 24–27 | Cylindrical, Very Long |
| 'Karmijn' | Purple-Violet (81B) | 12–15 | 2.0 | 26–29 | Campanulate, Medium Length |

The accompanying photographs of 'Milka' show a typical specimen plant of the new cultivar. The colors appearing in the photographs are as true as possible with color illustrations of this type.

Sheet 1 is a side view of 'Milka'.

Sheet 2 is a close-up of a flower of the new cultivar.

In the following description, color references are made to The Royal Horticultural Society Colour Chart (R.H.S.), except where general colors of ordinary significance are referred to. Color values were taken indoors under north light conditions in Bet Dagan, Israel.

Botanical classification:

*Species name.*—Aster Novi-Belgii L.

*Cultivar name.*—'Milka'.

Parentage:

*Male parent.*—Proprietary selection from the P Family.

*Female parent.*—Proprietary selection from the Butterfly family.

Propagation: The new cultivar maintains its distinguishing characteristics through successive reproduction by cuttings.

Inflorescence

A. Capitulum:

*Form.*—Convex.

*Type.*—Double.
*Diameter across face.*—24–27 mm.

B. Corolla of ray florets:
*Color* (*generally tonality from a distance of three meters*).—Blue.
*Color* (*upper surface*).—Violet RHS 85A
*Color* (*under surface*).—Same as upper surface.
*Size.*—14–16 mm in length and 2.0 mm in width.
*Shape.*—Narrowly elliptic, acute apex.
*Number of ray florets.*—128–164 per flower.

C. Corolla of disc florets: 'Milka' does not produce disc florets.

D. Reproductive organs:
*Androecium.*—Absent.
*Gynoecium.*—Present.

E. Buds:
*Size.*—7 mm diameter just before opening.
*Color.*—Color of flower petals as the bud opens is 85A.

Plant

A. General appearance: The height of 'Milka' is short to medium, depending on light; but under continuous (up to 17½ hours) long day-length conditions, plant height can reach 2 m; branching is dense, and there are many hairs on the stem.

B. Foliage:
*Color.*—Dark Green (RHS 137A–137B).
*Shape.*—Elliptic.
*Margin.*—Dentations on whole margin.
*Size.*—With regard to the following description, the first internode is found at the location of the first side flower under the top flower. Length: 5th Internode: 44–47 mm. 10th Internode: 71–76 mm. 15th Internode: 100–124 mm. 20th Internode: 125–146 mm. Width: 5th Internode: 4.0–6.0 mm. 10th Internode: 7.5–9.0 mm. 15th Internode: 11.0–14.0 mm. 20th Internode: 14.0–15.0 mm.

C. Stem:
*Length of internode.*—5th internode: 15–17 mm. 10th internode: 20–26 mm. 15th internode: 23–25 mm. 20th internode: 19–33 mm.
*Thickness of internode.*—5th internode: 1.9–2.1 mm. 10th internode: 3.0–3.5 mm. 15th internode: 3.5–4.2 mm. 20th internode: 4.5–5.0 mm.

D. Side branch:
*5th internode.*—53–67 mm. 10th internode: 76–97 mm. 15th internode: 100–153 mm. 20th internode: 164–206 mm.

E. Disease resistance: No abnormal disease problems have been noted to date. Accordingly, the disease resistance exhibited by this cultivar when compared to other known comercial aster varieties is not unique. However, the cultivar does appear to exhibit some resistance to tomato spotted wilt virus.

F. Fertility: 'Milka' does not produce pollen.

I claim:

1. A new and distinct variety of aster plant named 'Milka', as illustrated and described herein.

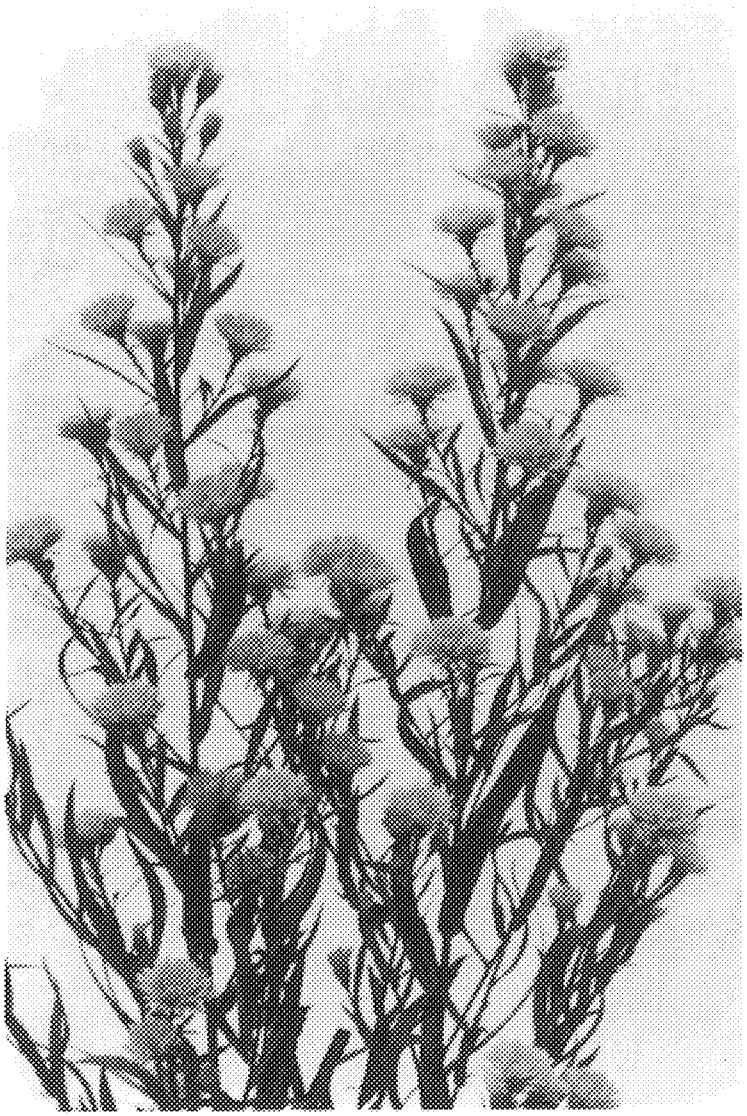

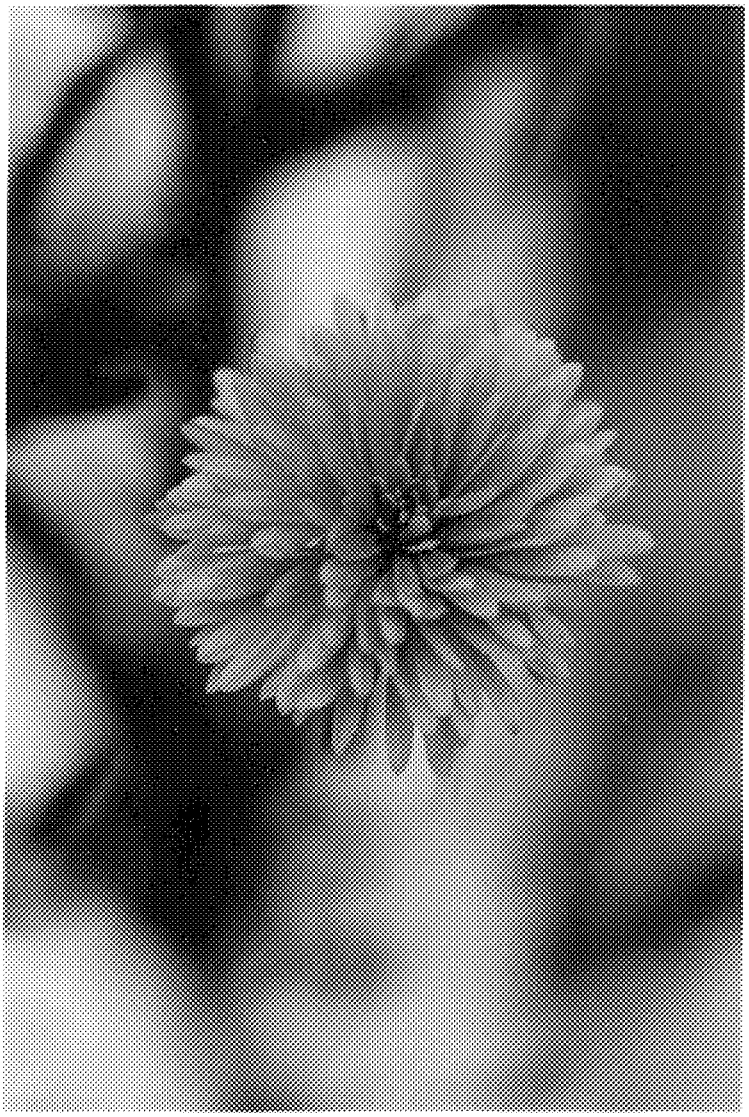

* * * * *